(12) United States Patent
Godfrey

(10) Patent No.: US 11,948,679 B2
(45) Date of Patent: *Apr. 2, 2024

(54) BLOOD MARKETPLACE SYSTEM AND METHOD

(71) Applicant: BloodSolutions, LLC, Dallas, TX (US)

(72) Inventor: Christopher Godfrey, Dallas, TX (US)

(73) Assignee: BLOODSOLUTIONS, LLC, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/080,417

(22) Filed: Dec. 13, 2022

(65) Prior Publication Data

US 2023/0114665 A1 Apr. 13, 2023

Related U.S. Application Data

(63) Continuation of application No. 16/859,314, filed on Apr. 27, 2020, now Pat. No. 11,551,809, which is a continuation of application No. 14/870,289, filed on Sep. 30, 2015, now Pat. No. 10,636,521.

(60) Provisional application No. 62/057,949, filed on Sep. 30, 2014.

(51) Int. Cl.
G16H 40/20 (2018.01)
G06Q 30/0201 (2023.01)
G06Q 30/0601 (2023.01)
G06Q 50/22 (2018.01)

(52) U.S. Cl.
CPC ......... G16H 40/20 (2018.01); G06Q 30/0201 (2013.01); G06Q 30/0635 (2013.01); G06Q 50/22 (2013.01)

(58) Field of Classification Search
CPC .............. G16H 40/20; G06Q 30/0201; G06Q 30/0635; G06Q 50/22
See application file for complete search history.

(56) References Cited

U.S. PATENT DOCUMENTS

2004/0133451 A1* 7/2004 Kleinschmidt ........ G16H 10/60
705/26.1
2014/0278499 A1* 9/2014 Bowman ............ G06Q 30/0601
705/2

* cited by examiner

*Primary Examiner* — Rachelle L Reichert
(74) *Attorney, Agent, or Firm* — Polsinelli PC

(57) ABSTRACT

A computerized system and method to provide a marketplace for real-time matching of a blood order to a blood supplier based on a variety of variables tracked by the system including real-time marketplace trend statistical analysis.

20 Claims, 15 Drawing Sheets

Orders — SUPPLY BLOOD PRODUCTS (04)

You Have 4 New Orders to fill  Expand All / Collapse All

| | DATE | TIME | ORDERED BY | DESCRIPTION | TRACKING # | STATUS |
|---|---|---|---|---|---|---|
| ▸ | 07/28/14 | 01:39pm | Children's Medical... | 5 RC | waiting... | 21:01 |
| ▸ | 07/26/14 | 04:25am | Children's Medical... | 17 RC | waiting... | 00:00 |
| ▸ | 07/23/14 | 04:00am | Brigham & Women... | 10 PLT | waiting... | 00:00 |
| ▸ | 07/23/14 | 03:58am | Brigham & Women... | 10 RC | waiting... | 00:00 |

Shipped & In Transit

No products are Shipped & In Transit

Delivered  Expand All / Collapse All

| | DATE | TIME | ORDERED BY | DESCRIPTION | TRACKING # | STATUS |
|---|---|---|---|---|---|---|
| ▸ | 07/22/14 | 11:15am | Children's Medical... | 1 RC, 10 FFP, 5 RC | 1238569741 | Delivered ✓ |
| ▸ | 07/22/14 | 10:31am | Children's Medical... | 5 Rc | 103569774 | Delivered ✓ |
| ▸ | 07/17/14 | 04:47pm | Brigham & Women... | 5 RC, 10 PLT, 1 RC | 0382020 | Delivered ✓ |
| ▸ | 07/17/14 | 03:37pm | Brigham & Women... | 5 RC, 5 PLT | 123-234 | Delivered ✓ |
| ▸ | 07/16/14 | 02:48pm | Brigham & Women... | 1 RC, 20 RC, 5 PLT | 12346-342-3839 | Delivered ✓ |
| ▸ | 07/15/14 | 02:31pm | Brigham & Women... | 10 RC, 5 PLT | 0924352 | Delivered ✓ |

Orders — PROCURE BLOOD PRODUCTS / SUPPLY BLOOD PRODUCTS (04)

Your Buying is turned off.
Please try back later or contact your admin...

Ordered

No products are Shipped & In Transit

In Transit

No products are currently In Transit

Received  Expand All / Collapse All

| | DATE | TIME | ORDERED BY | DESCRIPTION | TRACKING # | STATUS |
|---|---|---|---|---|---|---|
| ▸ | 07/21/14 | 05:23pm | Ryan Prater | 5 FFP, 5 FFP, 10 FFP | 128596932 | Received ✓ |
| ▸ | 07/21/14 | 05:19pm | Ryan Prater | 6 RC, 5 RC, 5 RC | 1834996363 | Received ✓ |

Fig. 2

Pricing Profiles                                    [EDIT PRICING PROFILE]

PROCURING BLOOD is turned off

Availability
⊙ Nationally  ○ State  ○ Local

SUPPLYING BLOOD is turned on

Availability
⊙ Nationally  ○ State  ○ Local

BLOOD PRODUCTS                                     Expand All / Collapse All

- Platelets – Single Donor Apheresis Leukoreduced  PLT
- Leukoreduced RBC  RC
- CRYO – CAF Singles  CRY
- CRYO – PCAF (Pool)  PCRY
- PLASMA – Single Unit  FFP
- PLASMA – Double Unit  AFFP
- Leukoreduced Whole Blood  WB

[EDIT PRICING PROFILE]

*Fig. 3*

Pricing Profiles

[EDIT PRICING PROFILE]

PROCURING BLOOD is turned off
Availability: ● Nationally ○ State ○ Local

SUPPLYING BLOOD is turned on
Availability: ● Nationally ○ State ○ Local

BLOOD PRODUCTS

Expand All / Collapse All

▸ Platelets – Single Donor Apheresis Leukoreduced  PLT

| ABO TYPE | PROCURE PRICE PER UNIT | SUPPLY PRICE PER UNIT | UNITS AVAILABLE |
|---|---|---|---|
| O+ | $ – | $ 485 | 990 |
| O– | $ – | $ 485 | 995 |
| A+ | $ – | $ 485 | 1000 |
| A– | $ – | $ 485 | 990 |
| B+ | $ – | $ 485 | 1000 |
| B– | $ – | $ 485 | 990 |
| AB+ | $ – | $ 485 | 990 |
| AB– | $ – | $ 485 | 1000 |
| CMV Negative | + $ – added | + $ – added | |
| Irradiated | + $ – added | + $ – added | |
| Age | at least – days left | at least 3 days left | |

▸ Leukoreduced RBC  RC
▸ CRYO – CAF Singles  CRY
▸ CRYO – PCAF (Pool)  PCRY
▸ PLASMA – Single Unit  FFP
▸ PLASMA – Double Unit  AFFP
▸ Leukoreduced Whole Blood  WB

*Fig. 4*

Orders

| PROCURE BLOOD PRODUCTS | SUPPLY BLOOD PRODUCTS |

CREATE NEW ORDER

Ordered

Expand All / Collapse All

| DATE | TIME | ORDERED BY | DESCRIPTION | TRACKING # | STATUS |
|---|---|---|---|---|---|
| 07/26/14 | 01:39pm | Chris Godfrey | 5 RC | waiting... | Ordered |
| 07/26/14 | 04:26pm | Chris Godfrey | 17 RC | waiting... | Ordered |

In Transit

No shipments are currently In Transit

Received

Expand All / Collapse All

| DATE | TIME | ORDERED BY | DESCRIPTION | TRACKING # | STATUS |
|---|---|---|---|---|---|
| 07/22/14 | 11:15am | Chris Godfrey | 1 RC, 5 RC, 10 FFP | 1238569741 | Received |
| 07/22/14 | 10:31am | Chris Godfrey | 5 RC | 103569774 | Received |
| 07/17/14 | 04:47pm | Chris Godfrey | 10 PLT, 5 RC, 1 RC | 0382020 | Received |

*Fig. 7*

BLOOD MARKETPLACE SYSTEM AND METHOD

CROSS-REFERENCE TO RELATED APPLICATION

This application is a continuation of and claims priority to U.S. application Ser. No. 16/859,314, filed Apr. 27, 2020, which is a continuation of and claims priority to U.S. application Ser. No. 14/870,289, filed Sep. 30, 2015, which claims priority to U.S. Provisional Application No. 62/057,949 filed Sep. 30, 2014. Each of these applications is incorporated by reference in its entirety herein.

FIELD

The presently disclosed technology relates generally to a computer-based marketplace for blood, and more particularly, to a system and method to record and track various variables for blood, assess demand for blood, provide fulfillment for blood orders, and ensure even distribution of supply across the system.

BACKGROUND

Blood is a bodily fluid that delivers a variety of necessary substances to cells in a body including oxygen and transports metabolic waste away from the cells of the body. A blood transfusion is, in many cases, a life-saving procedure used to address trauma cases and various medical conditions, for example, to replace lost components of the blood.

Obtaining blood to perform a blood transfusion present a variety of complex issues. For instance, it is necessary to ensure proper blood type. There are thirty-three recognized human blood groups with two, i.e., ABO and the RhD antigen, determining blood type, i.e., A, B, AB, and O, with a positive "+" or − indicating RhD status. O− blood is generally compatible for use in combination with any other blood type. As a result, O− blood is often overused and in short supply.

It is also necessary to ensuring proper blood ratio. Although early transfusions used whole blood, i.e., blood having all of its components, modern transfusions commonly use only components of blood in various predetermined ratios. The components of blood include red blood cells, white blood cells, platelets, plasma, and cryoprecipitate. In a massive trauma resuscitation scenario requiring more than ten units of blood, higher ratios of fresh frozen plasma and platelets relative to packed red blood cells are delivered to a patient. Use of a lesser amount of red blood cells is associated with a lower risk of infection.

It is also necessary to ensure proper handling of blood to minimize risk of infection and timely receive blood, for example, during unscheduled massive trauma resuscitation scenarios or during scheduled surgical procedures to address a medical condition. Such handling must be carried out promptly for ideal transfusion efficacy. Platelets may only be stored for five days, and packed red blood cells are typically stored for only forty-two days in a refrigerated state versus a frozen state using a first-in first-out inventory management system.

Thus, when there is a demand for blood, whether scheduled or unscheduled, it is desirable that an administrator be able to quickly identify one or more blood units to meet the demand in view of ideal blood ratio, ideal blood type, and ideal number of units, and expedite ordering and delivery of such to a location, e.g., a hospital of a patient, thereby minimizing risk of infection and maximizing efficacy. Conventional blood management systems are deficient in this regard. No conventional blood management system provides real-time matching of blood units or is able to categorize blood units based on components of blood, ratio, and type. Further, no conventional blood management system provides an automated combining of different blood units from different locations to meet an order placed by a user for a single use or patient. Still further, no conventional blood management system tracks geographic restraints, tracks and prices units of blood in view of demand, or tracks price tolerances, e.g., of an ordering entity or of a supplier. Rather, such conventional systems are limited to basic online order and fulfillment. For instance, U.S. patent application Ser. Nos. 12/973,511 and 14/211,417, which are incorporated by reference herein in their entireties, are generally limited to order entry and fulfillment.

Thus, there exists a need for system and method that does not suffer from the aforementioned deficiencies, satisfies the aforementioned needs, and is efficient, economical, and easy to implement and utilize.

SUMMARY

In response to the aforementioned needs, the present application describes a computerized system and method that provides a user with an online portal for real-time matching of a blood order to a blood supplier based on a variety of variables tracked by the system including real-time marketplace trend statistical analysis.

In accordance with an aspect of the present inventive concept, a system is provided that provides real-time matching of blood units and is configured to categorize blood units based on components of blood, ratio, and type, to automate combining of different blood units from different locations to meet an order placed by a user for a single use or patient, to track geographic restraints, to track and price units of blood in view of demand, and to track price tolerances, e.g., of an ordering entity or of a supplier.

In accordance with an aspect of the present inventive concept, a system is provided that is configured to enable a user, e.g., a hospital administrator, a lab professional, or a buyer of blood, to populate and fully articulate an order for blood, e.g., based on one or more components, and match the order to one or more suppliers of blood.

In accordance with an aspect of the present inventive concept, a system is provided that is configured to enable a user, e.g., a hospital administrator, a lab professional, or a supplier of blood, to populate and fully articulate a supply of blood, e.g., based on one or more components, and warehouse the supply of blood, e.g., collect, store, and/or maintenance data associated with the supply of blood, to enable searching, identification, and/or matching of the supply of blood to an order for blood.

In accordance with an aspect of the present inventive concept, a system is provided that is configured to enable a user, e.g., a supplier of blood and/or a buyer of blood, to track an order of blood from order, transport, and delivery, e.g., time, date, geographic location, one or more factors associated with the blood, e.g., a storage temperature of the blood, at every step therebetween.

In accordance with an aspect of the present inventive concept, a system is provided that is configured to provide a user with price data in real time associated with blood based on one or more factors associated with the blood, e.g., demand and supply.

The aforementioned may be achieved in one aspect of the present inventive concept by providing a computerized marketplace system for blood. The system may include a memory configured to store data related to units of blood, a supplier portal configured to allow a first user to input one or more variables related to a supply of blood, an order portal configured to allow a second user to input an order with one or more variables related to a demand for blood, and/or a processor configured to (i) deduce variables related to the units of blood based on at least the one or more variables related to the supply of blood, (ii) process the order based on logic and by matching one or more of the variables related to the units of blood and one or more of the additional variables related to the units of blood to one or more of the variables related to the demand for blood, and/or (iii) display a match to the second user with corresponding information related to the match via the order portal.

The system may be configured to deduce additional variables related to the units of blood based on (i) the one or more of the variables related to one of the units of blood, and/or (ii) market data obtained from a database. The database may be configured to (i) receive the market data from market participants, and (ii) calculate one or more trends based on the market data. The variables may be related to the demand for blood input by the second user include one or more of (i) a price tolerance of an ordering entity, (ii) a geographic location of the ordering entity, (iii) other orders requested by the ordering entity, and/or (iv) a deadline of the ordering entity. The variables may be related to the demand for blood input by the second user include one or more of (i) a price tolerance of an ordering entity, (ii) a geographic location of the ordering entity, (iii) other orders requested by the ordering entity, and/or (iv) a deadline of the ordering entity.

The aforementioned may be achieved in another aspect of the present inventive concept by providing a computerized method to buy blood. The method may include the steps of accessing a portal in communication, and/or submitting an order for one or more of the units via the portal. The system may have (i) a memory configured to store one or more variables related to units of blood, and (ii) a processor configured to deduce additional variables related to the units of blood based on the one or more variables related to one of the units of blood. The processor may be configured to (i) process the order by matching one or more of the variables related to the units of blood and one or more of the additional variables related to the units of blood to one or more of the variables related to the demand for blood, and (ii) cause a match to be displayed to the second user with corresponding information related to the match via the portal.

The method may further include the step of allowing a first user to input one or more of the variables related to one of the units of blood via a second portal. The method may further include the step of allowing a second user to input an order with variables related to a demand for blood via an order portal.

The aforementioned may be achieved in another aspect of the present inventive concept by providing a method of administering blood to a patient via a computerized system. The method may comprise the steps of extracting blood from a blood donor at a blood-donation entity, processing one or more components of the blood at the blood-donation entity, packaging the one or more components of the blood at the blood-donation entity, and/or accessing a computerized system and inputting information associated with the one or more components of the blood to a database associated with the computerized system. The information may include one or more of (i) a number of units of the one or more components of the blood, (ii) a price per unit of the one or more components of the blood, and (iii) a geographic location of the one or more components of the blood.

The method may further include the step of receiving an order for the one or more components of the blood with shipping information via the computerized system, the shipping information including a geographic location associated with the patient, and/or shipping the one or more components of the blood to the geographic location associated with the patient for administering to the patient. The system may be configured to match the order with one of a plurality of suppliers of blood based on a plurality of factors. The method may further include the step of setting the price per unit of the one or more components of the blood based on trend information provided by the computerized system. The trend information may include historic price information associated with the one or more components of the blood from one or more prior orders filled using the computerized system.

Additional aspects, advantages, and utilities of the present inventive concept will be set forth in part in the description which follows and, in part, will be obvious from the description, or may be learned by practice of the present inventive concept.

The foregoing is intended to be illustrative and is not meant in a limiting sense. Many features and subcombinations of the present inventive concept may be made and will be readily evident upon a study of the following specification and accompanying drawings comprising a part thereof. These features and subcombinations may be employed without reference to other features and subcombinations.

BRIEF DESCRIPTION OF THE DRAWINGS

Embodiments of the present inventive concept are illustrated by way of example in which like reference numerals indicate similar elements and in which:

FIG. 2 illustrates an example display provided to a user via a display of a computing device of the user according to an embodiment of the present inventive concept;

FIG. 3 illustrates another example display provided to a user via a display of a computing device of the user according to an embodiment of the present inventive concept;

FIG. 4 illustrates another example display provided to a user via a display of a computing device of the user according to an embodiment of the present inventive concept;

FIG. 7 illustrates another example display provided to a user via a display of a computing device of the user according to an embodiment of the present inventive concept;

Figure 1:
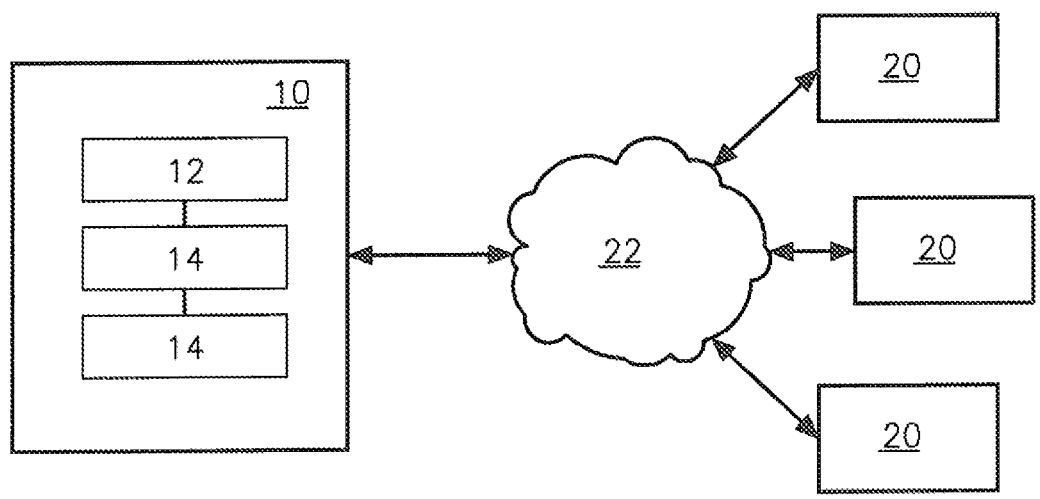
FIG. 1 illustrates an example system with communication pathways according to an embodiment of the present inventive concept.
Figure 5:
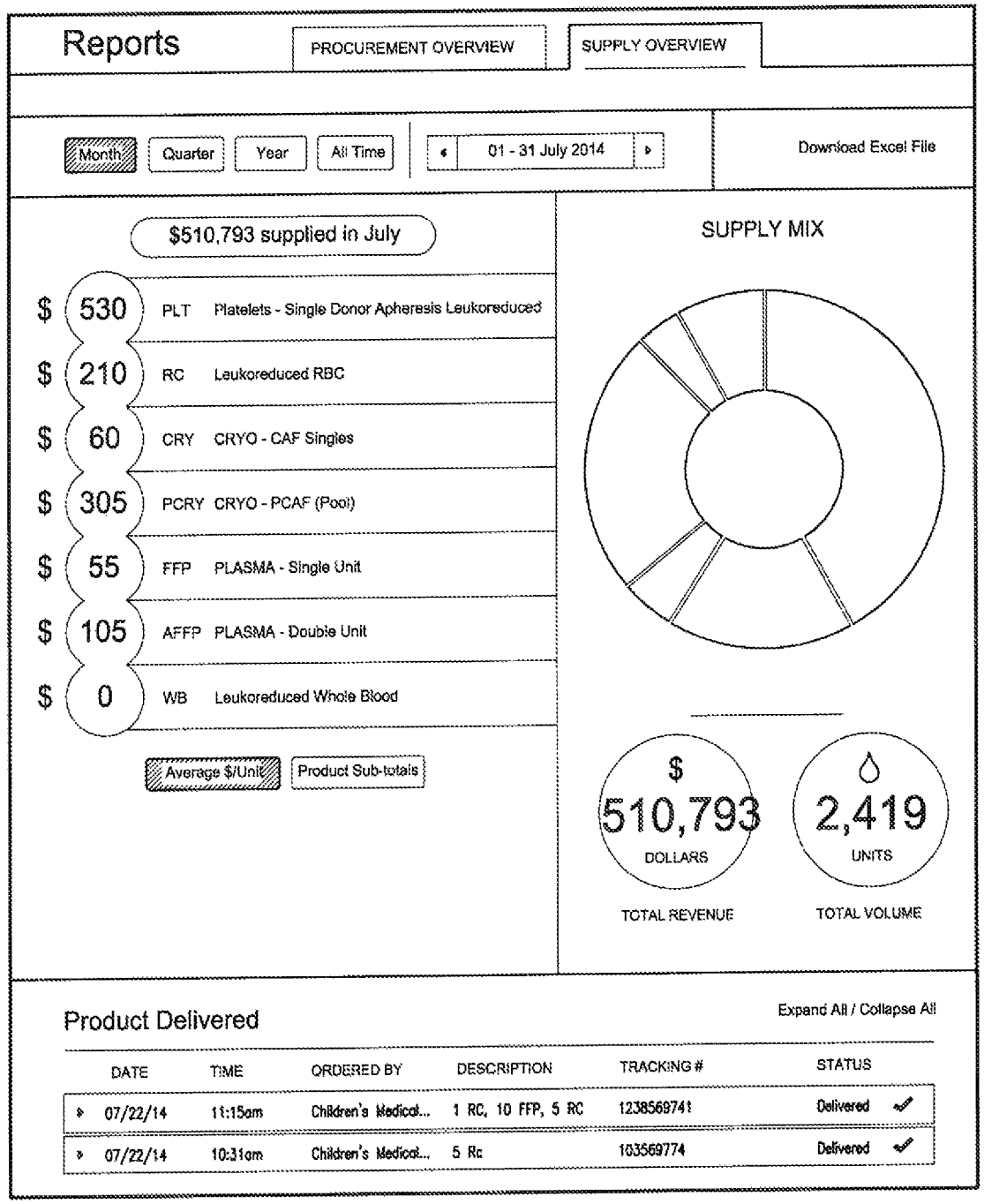
FIG. 5 illustrates another example display provided to a user via a display of a computing device of the user according to an embodiment of the present inventive concept.
Figure 6:
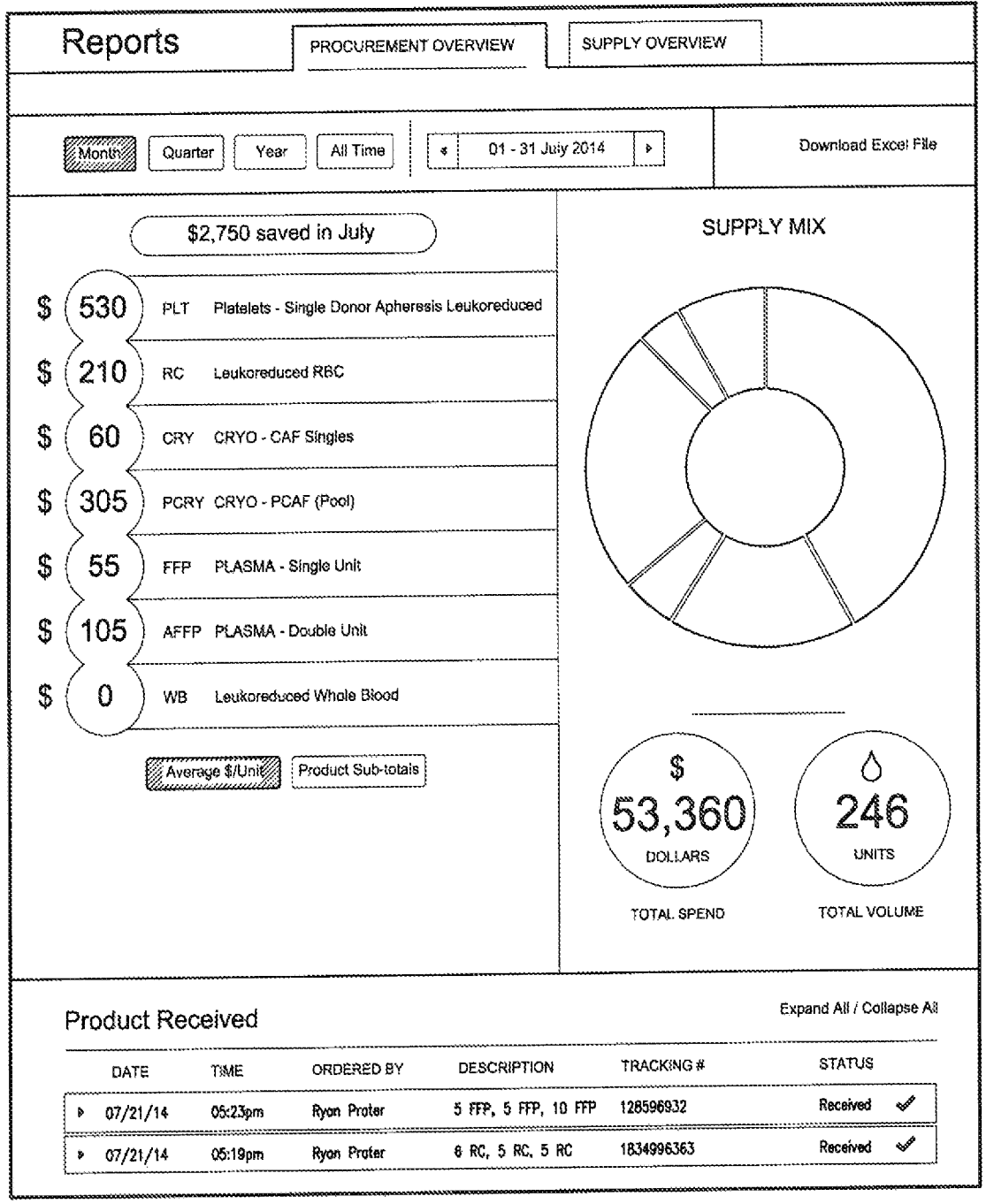
FIG. 6 illustrates another example display provided to a user via a display of a computing device of the user according to an embodiment of the present inventive concept.

The drawing figures do not limit the present inventive concept to the specific embodiments disclosed and described herein. The drawings are not necessarily to scale, emphasis instead being placed on clearly illustrating principles of certain embodiments of the present inventive concept.

DETAILED DESCRIPTION

The following detailed description references the accompanying drawings that illustrate various embodiments of the present inventive concept. The illustrations and description are intended to describe aspects and embodiments of the present inventive concept in sufficient detail to enable those skilled in the art to practice the present inventive concept. Other components can be utilized and changes can be made without departing from the scope of the present inventive concept. The following detailed description is, therefore, not to be taken in a limiting sense. The scope of the present inventive concept is defined only by the appended claims, along with the full scope of equivalents to which such claims are entitled.

I. Terminology

In the following detailed description, terminology is used to describe features of the present inventive concept. For example, references to terms "one embodiment," "an embodiment," or "embodiments" mean that the feature or features being referred to are included in at least one aspect of the present disclosure. Separate references to terms "one embodiment," "an embodiment," or "embodiments" in this description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the present inventive concept may include a variety of combinations and/or integrations of the embodiments described herein. Additionally, all aspects of the present disclosure as described herein are not essential for its practice.

Further, in certain situations, the term "logic" refers to hardware, firmware, software, and/or a combination thereof that is configured to perform one or more functions including, but not limited to, those functions of the present inventive concept specifically described herein or are readily apparent to those skilled in the art in view of the description. Such logic may include circuitry having data processing and/or storage functionality. Examples of such circuitry may include, but are not limited to, a microprocessor, one or more processors, e.g., processor cores, a programmable gate array, a microcontroller, an application specific integrated circuit, a wireless receiver, transmitter and/or transceiver circuitry, semiconductor memory, or combinatorial logic.

Logic may be in the form of one or more software modules, such as executable code in the form of an executable application, an application programming interface (API), a subroutine, a function, a procedure, an applet, a servlet, a routine, source code, object code, a shared library/dynamic load library, or one or more instructions. These software modules may be stored in any type of a suitable non-transitory storage medium, or transitory storage medium, e.g., electrical, optical, acoustical or other form of propagated signals such as carrier waves, infrared signals, or digital signals. Examples of non-transitory storage medium may include, but are not limited or restricted to a programmable circuit; a semiconductor memory; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the executable code is stored in persistent storage.

The term "content" generally refers to information transmitted as one or more messages, where each message(s) may be in the form of a packet, a frame, an Asynchronous Transfer Mode "ATM" cell, or any other series of bits having a prescribed format. The content may be received as a data flow, namely a group of related messages, within ingress data traffic. Content may include one or more types of data such as, but not limited to, text, software, images, audio, metadata and/or other digital data. One example of content may include web content, or any data traffic that may be transmitted using a Hypertext Transfer Protocol (HTTP), Hypertext Markup Language (HTML) protocol, or may be transmitted in a manner suitable for display on a Web browser software application. Another example of content includes electronic mail or email, which may be transmitted using an email protocol such as Simple Mail Transfer Protocol (SMTP), Post Office Protocol version 3 (POP3), or Internet Message Access Protocol (IMAP4). A further example of content includes an Instant Message, which may be transmitted using Session Initiation Protocol (SIP) or Extensible Messaging and Presence Protocol (XMPP) for example. Yet another example of content includes one or more files that are transferred using a data transfer protocol such as File Transfer Protocol (FTP) for subsequent storage on a file share.

The term "computerized" generally represents that any corresponding operations are conducted by hardware in combination with software and/or firmware.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As the present inventive concept is susceptible to embodiments of many different forms, it is intended that the present disclosure be considered as an example of the principles of the present inventive concept and not intended to limit the present inventive concept to the specific embodiments shown and described.

II. General Architecture

Turning to FIG. 1, the present general inventive concept provides a computerized system 10 to order or buy blood and to supply blood, and a method of using the system 10 by various users, e.g., a buyer of blood and a supplier of blood. It is foreseen that the system 10 may be used to manage, procure, and/or supply other commodities such as tissue and/or bone without deviating from the scope of the present inventive concept. The system 10 generally includes a processor 12, a memory 14 containing logic for the processor 12, and one or more servers 16, which are in communication with each other. The server 14 provides an online portal that is accessible via a computing device 20 of a user that is connected to a communication network 22 via a wired or wireless connection. The network 22 can be the Internet, an intranet, or another wired and/or wireless communication network. The system 10 is secure, thereby only permitting access thereto after the user has entered credential information via the portal and the system 10 confirms via the processor 12 that the user is authorized to access the system 10 using the credential information.

It is foreseen that depending on a user type, the system 10 may be configured to cause to be displayed one of a plurality of screens via a display of the computing device 20 after the user has been authorized to access the system 10. In the preferred embodiment, however, after the user has been authorized to access the system 10, a display is provided to the user, such as that illustrated by FIG. 2, that allows the user to select whether the user would like to either procure one or more units of blood or supply one or more units of blood, i.e., order or supply blood. It is foreseen that the user may input the selection via the display of the computing device, e.g., a touch-screen display, a keyboard, a mouse, a voice command, and/or other input receiver associated with the computing device 20.

Simultaneous with the aforementioned display, the system 10 is configured to display shipping information to the user associated with any pending and/or past orders for blood, whether ordered by the user or supplied by the user. It is foreseen that such shipping information may include, but is not limited to, order tracking, i.e., a present, past, and/or future geographic location of blood with associated time and/or date information, and/or one or more factors associated with the blood, e.g., a storage temperature of the blood, at every step during transport of the blood. Other shipping information may include a date and time delivered and/or ordered a name of a buyer and/or supplier, a description of the blood, a tracking number, and a status, e.g., ordered, sent, in transit, delivered, and/or received. The status for the shipping information may allow the user to indicate whether a shipment was received and a condition of the shipment upon receipt. For instance, the user may "flag" the shipment and include comments regarding the shipment for review by one or more other users of the system, e.g., a sender of the shipment, an administrator of the system or entity of the sender, and/or another potential purchaser of goods shipped via the shipment. For instance, the user may indicate a container of the shipment was damaged, the shipment was not kept at a proper temperature to adequately preserve the shipment, and/or the like.

Turning to FIG. 3, the system 10 is configured to display one or more pricing profiles to the user based on one or more units of blood that are available to be ordered and/or past orders of blood that occurred within a predetermined period of time, e.g., one to a plurality of days, months, and/or years. The system 10 is configured to allow the user to input information associated with one or more units of blood available to be supplied via the system 10. The system 10 is configured to allow the user to edit existing information associated with one or more units of blood.

Each pricing profile includes geographic information for a corresponding unit of blood. In this manner, the user, whether buying or supplying blood, can target blood based on proximity of the blood to the user, e.g., a local level, a state level, a national level, and/or a global level, and obtain a value of blood based on geography, supply, and demand. For purposes herein, local means within five miles of the user, state means within the state of the user, national means within the nation of the user, and global means anywhere. Each pricing profile further includes blood product information, e.g., component information associated with the blood. For instance, each pricing profile indicates whether the blood is platelets, e.g., a single donor apheresis leukoreduced or "PLT", leukoreduced RBC or "RC", CRYO—CAF singles or "CRY", CRYO—PCAF (Pool) or "PCRY", plasma-single unit or "FFP", or plasma—double unit or "AFFP", leukoreduced whole blood or "WB" and/or the like.

The user is able to select a desired blood product via the computing device 20, which causes a drop-down menu of additional data to be displayed, as illustrated by FIG. 4. As illustrated in this scenario, the user selected a supply of PLT available at a national level, which causes additional data associated with the blood product PLT to be displayed, e.g., ABO type, procure price per unit, supply price per unit, units available to the user for procurement, cytomegalovirus or CMV negative, whether one or more of the blood units have been irradiated, an age of the one or more units, antigen data, and/or the like. Using this display of the system 10, the user is able to place an order, which causes the system to attempt to fill the order via one or more suppliers used in view of current demand and criteria set by the user for the order. The user may edit various criteria, e.g., price and/or days until expiration in attempt to facilitate filling of the order by the system. It is foreseen that the user may simultaneously select both procuring blood and supplying blood with either or both at any one or more of the aforementioned levels without deviating from the scope of the present inventive concept.

The system 10 maintains a profile for the user to track and store, via the memory a variety of information including, but not limited to a hospital and/or blood bank associated with the user, price tolerance data associated with the information of the user, and/or order/supply history associated with the user via the memory 14. As illustrated by FIGS. 5-8, the system 10 is configured to deliver a variety of reports to the user upon request of the user with predefined data. The data may be historic data, real time data, and/or future data using a predictive algorithm and one or more of the historic data and real time data based on one or more trends tracked by the system 10. The historic data may be include a defined time period selectable by the user, e.g., a specific month, a specific quarter of a year, a specific year, or total historic data for all time. The report is able to be generated based on one or more specific blood products, e.g., PLT, RC, CRY, PCRY, FFP, AFFP, and/or WB, and include a total supplied of all of the blood products and/or a total supplied for each of the blood products, each with associated pricing information and associated averages. The report may include total revenue of the user, total spend of the user, total volume processed by the user, and associated shipping information. The report may include one or more graphs to quickly convey information to the user, e.g., a supply mix and/or a procurement mix. The report may include a total savings of the user based on a difference between a user's set or desired maximum or minimum price and an actual purchase or sell price, respectively, including any add-ons, e.g., irradiated and/or the like. For instance, the report may indicate that the user as saved via the written statement "$2,750 saved in July."

Various displays are provided by the system 10 to the computing device 20 of the user with detailed information regarding one or more blood orders. As illustrated, the system 10 indicates the user has placed orders for 5 RC and 17 RC, i.e., an order for five red cell units and an order for seventeen red cell units, the system 10 is awaiting tracking number information and no shipments are currently in transit, and information for orders already received by the user. The system 10 allows the user to specify every aspect of the order based on real time information when placing an order for blood. The system 10 allows the user to specify components, ABO/RH, quantity, as well as additional processes such as CMV negative, irradiated, and/or antigens. The system 10 allows the user to specify a maximum monetary price per unit and/or a maximum age per unit, i.e., an age calculated from a time of donation of the blood via a blood donor at a blood bank or hospital. The system 10 allows the user to associate urgency information with each order. For instance, the user may select one of a rush or "stat" order, e.g., ship entire order within one hour of acceptance of order, a stock order, e.g., ship entire order within twenty-four hours of acceptance of order, or a standing order, e.g., ship periodically at a set date, e.g., on each first day of the month. For purposes herein, "acceptance of order" means upon generation of a notification to a supplier that an order has been filled. Thus, it is necessary that the supplier take steps to ensure it is able to process a stat order via sufficient personnel at any hour. It is foreseen that the system may include a selectable option to allow the supplier to accept or not accept one or more order types, e.g., stat, stock, and/or standing, during one or more specific periods of time(s) and/or day(s), e.g., on weekends, after and/or before specific hours without deviating from the scope of the present inventive concept. It is also foreseen that any order data may be provided via a menu, e.g., a drop-down menu, to the user for selection of the user via the computing device 20 without deviating from the scope of the present inventive concept. The system 10 also provides the user, for each blood product, an expiration date or time period during which each of the blood products should be used, i.e., administered to a patient.

The system 10 may be configured to set a value for a blood product based on expiration date. For instance, the system 10 may be configured to price or value blood products with fewer days remaining until expiration as less valuable as blood products with relatively more days remaining until expiration. The system 10 may be config-ured to factor in other factors that could affect use of the blood products before expiration, e.g., shipping time in view of distance between supplier and recipient. Thus, identical blood products from different suppliers may have different values if one supplier is closer to the recipient than the other supplier, i.e., the blood product from the supplier that is closer to the recipient may have a higher value than the blood product from the supplier that is further away from the recipient. It is foreseen that, if the user desires to order blood for immediate use, the user may be able to save money by ordered the blood with fewer days remaining until expiration. The system 10 may suggest one or more alternatives to the user to allow the user to save on blood products. In this manner, the system 10 is advantageously configured to avoid waste.

Figure 9:
FIG. 9 illustrates another example display provided to a user via a display of a computing device of the user according to an embodiment of the present inventive concept.
Figure 10:
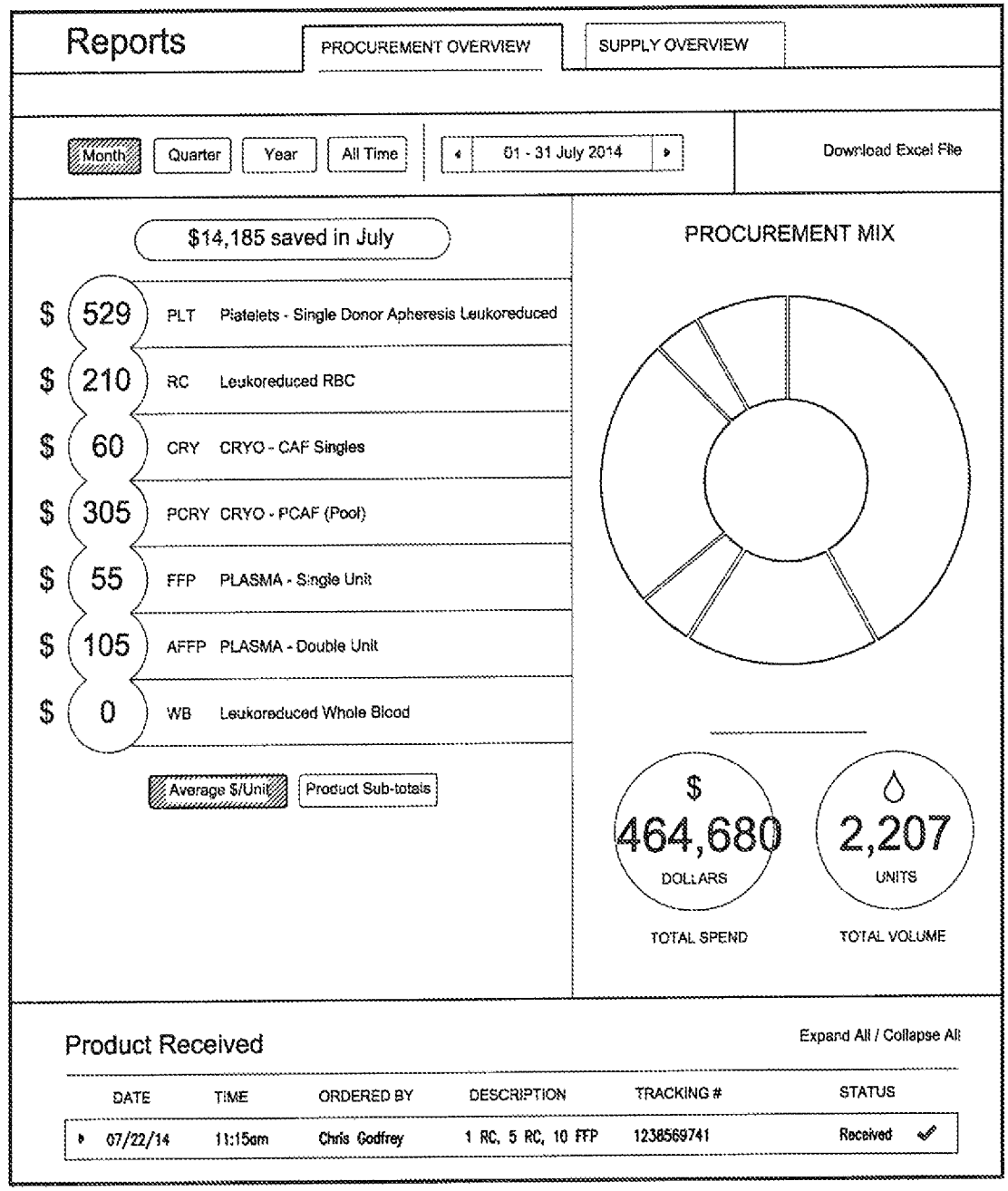
FIG. 10 illustrates another example display provided to a user via a display of a computing device of the user according to an embodiment of the present inventive concept.
Figure 11:
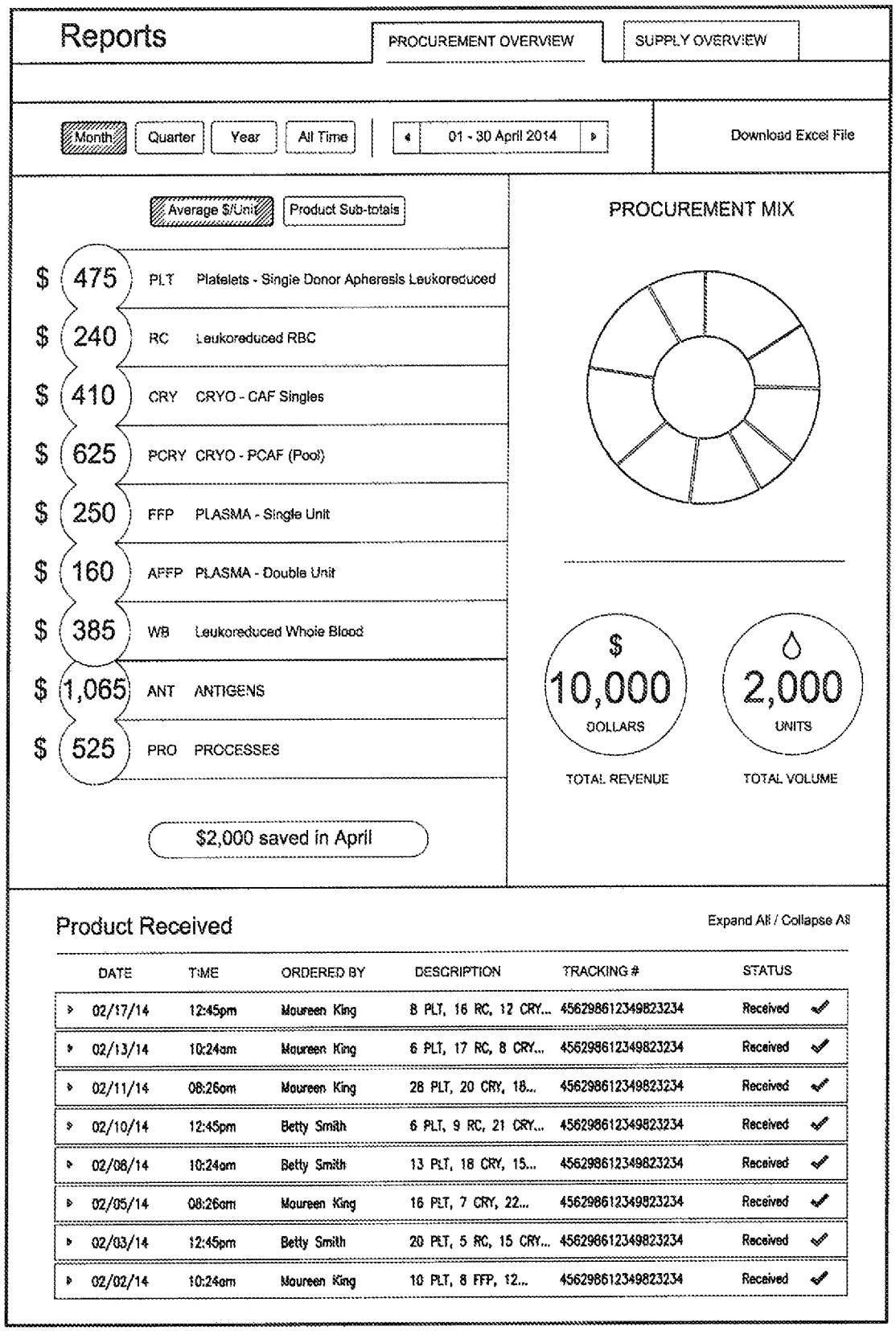
FIG. 11 illustrates another example display provided to a user via a display of a computing device of the user according to an embodiment of the present inventive concept.
Figure 12:
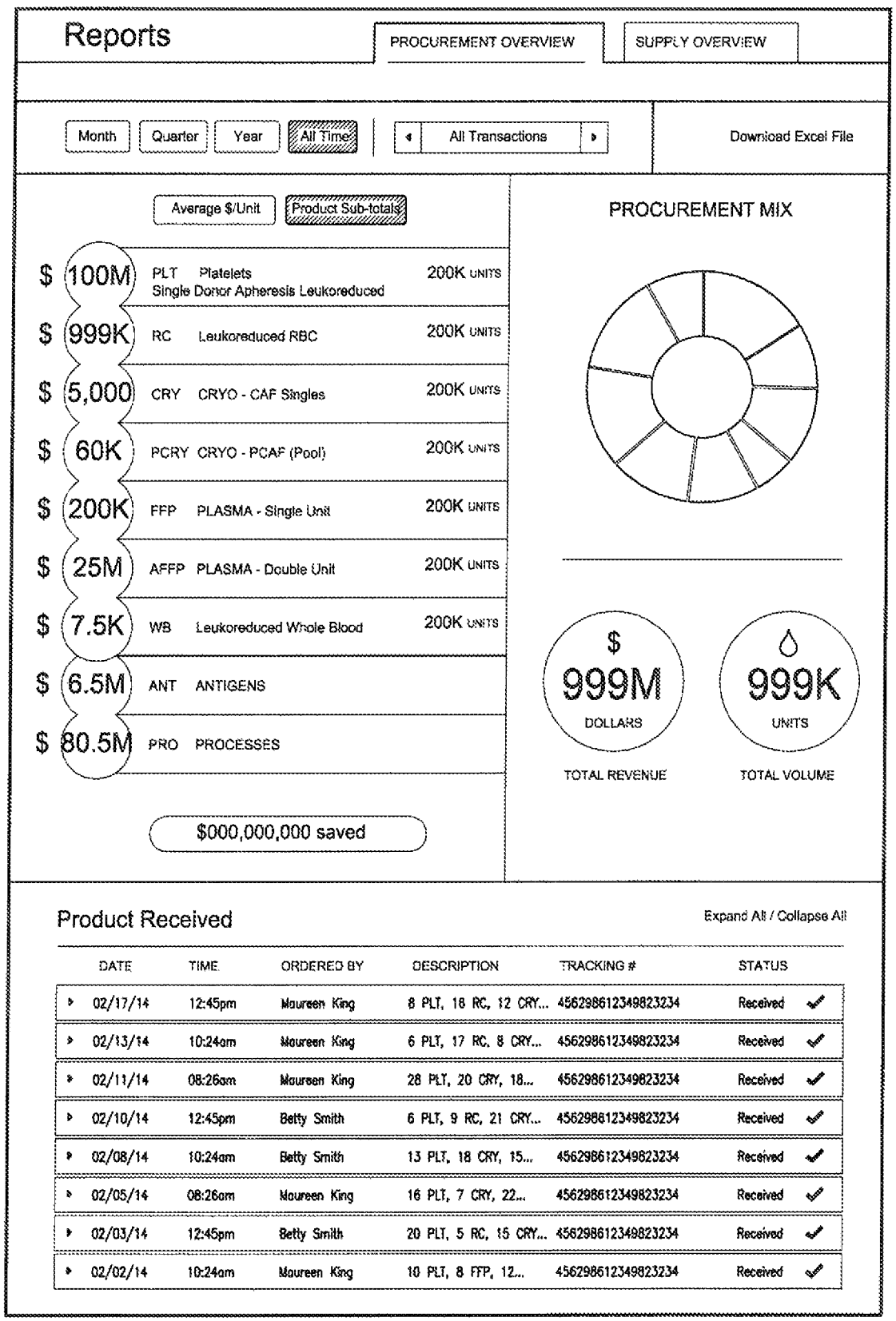
FIG. 12 illustrates another example display provided to a user via a display of a computing device of the user according to an embodiment of the present inventive concept.
Figure 13:
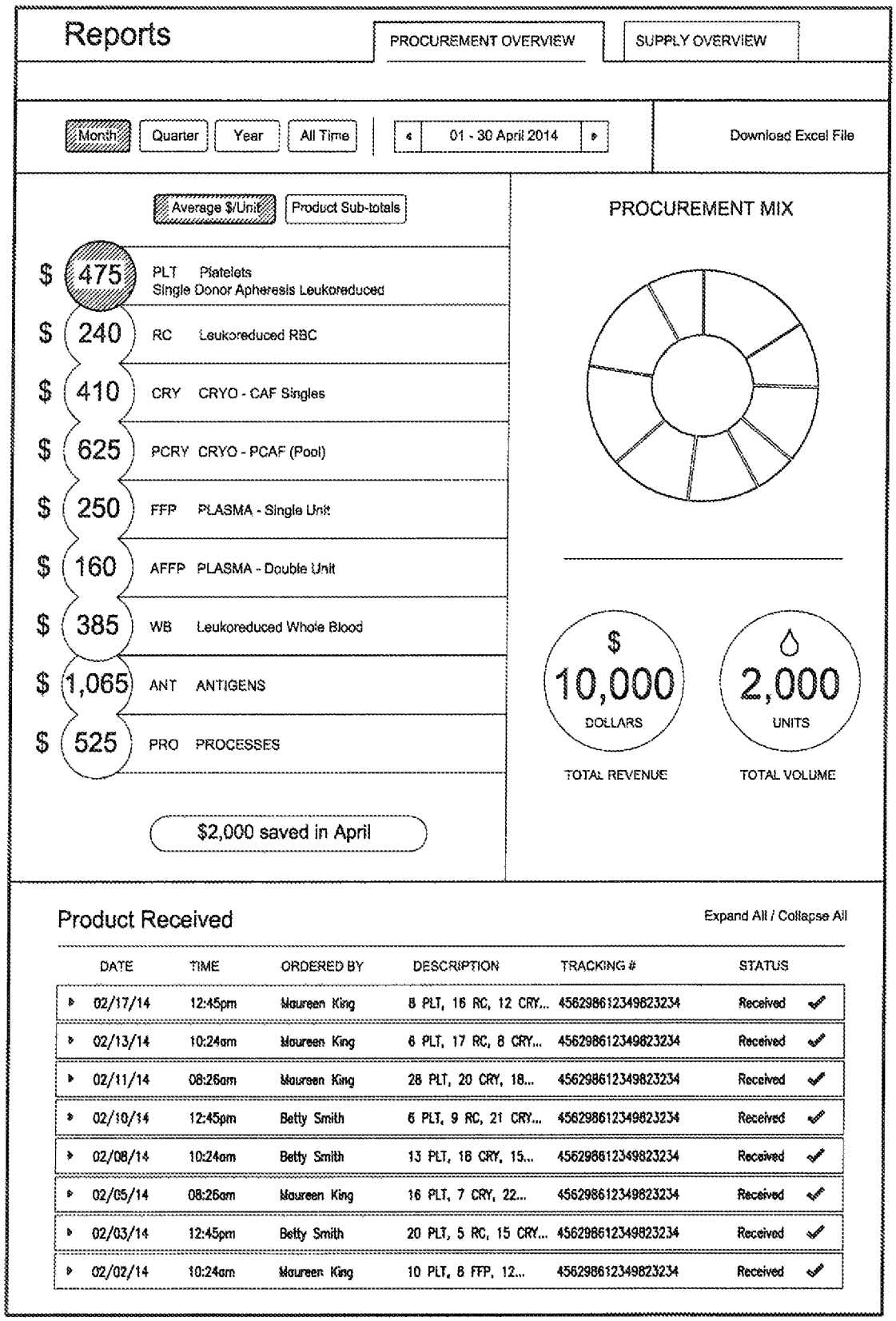
FIG. 13 illustrates another example display provided to a user via a display of a computing device of the user according to an embodiment of the present inventive concept.
Figure 14:
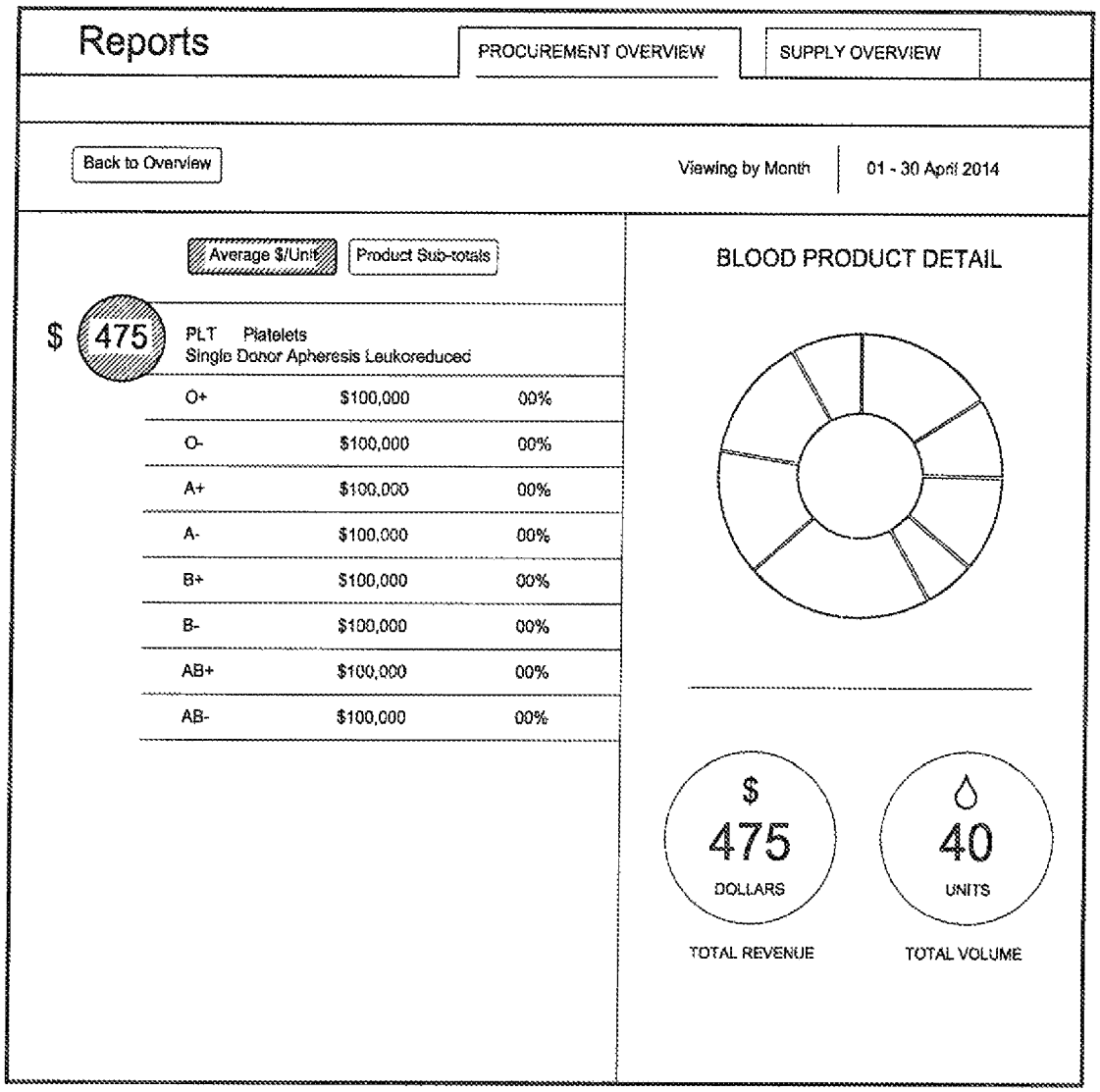
FIG. 14 illustrates another example display provided to a user via a display of a computing device of the user according to an embodiment of the present inventive concept.

In use, the user inputs information associated with an order for blood into the system 10 via the computing device 20 and places the order. Upon placement of the order, the system 10 executes a simultaneous search of a variety of different blood supplier information and associated blood supply for each supplier to identify a match, i.e., an exact match or a best match, to the order for blood based on the information input by the user. When the match is identified, the match is displayed by the system 10 to the user via the computing device 20 and the order is transmitted to the supplier of the match via the computing device 20 of the supplier of the match, as illustrated by FIG. 9. The system 10 indicates that the order has been filled by displaying information associated with the filled order, e.g., supplier information, maximum purchase price, actual price paid per unit, and savings, if any, based on maximum purchase price and actual price paid.

The system 10 allows the user, e.g., the buyer and/or the supplier, to select a shipping method as desired based on price, speed, or like other considerations, and provides automatic updates to the user to indicate status of the shipment, e.g., shipped, in transit, delivered, and/or received. The system 10 automatically generates reporting information for the user to help the user document the transaction. Similar to the report to a supplier generated by the system 10 and illustrated by FIG. 5, FIGS. 10-14 illustrate various reports to a buyer generated by the system 10, which provides similar information. It is foreseen that the user can be both the supplier and the buyer, and the user need only make a selection, e.g., a tab selection via the computing device 20, to receive and view either or both reports. The system 10 provides a plurality of selectable levels of information related to various components of blood, as illustrated by FIGS. 10-14, which are selected by the user via the computing device of the user. As illustrated, the user is allowed to select one or more of (i) a product subtotal; (ii) a product; and (iii) a subset of the product. The user can select any one or more of the products and/or subsets, but for illustration purposes, the user selects PLT and B−. The mix information generated by the system 10, i.e., color-coded pie charts associated with the procurement mix and the supply mix, advantageously allows the user to fully understand past market trends and better anticipate future market trends with respect to blood.

Figure 15:
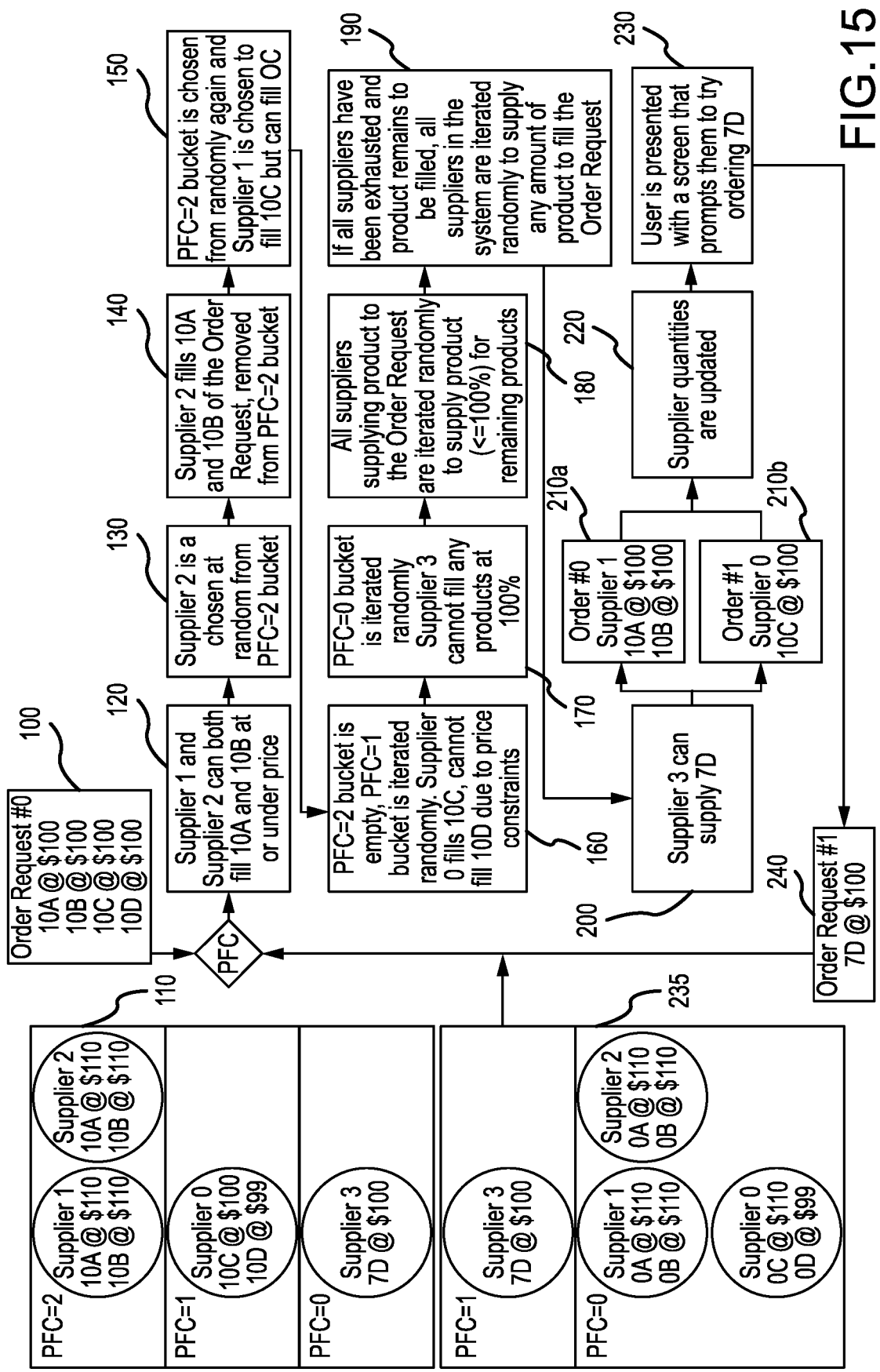
FIG. 15 illustrates a flowchart of an example use of the system and method according to an embodiment of the present inventive concept.

Turning to FIG. 15, an exemplary use scenario of the system 10 using logic, e.g., contained in the memory 14 and via the processor 12, is illustrated. At Step 100, the user submits an order request #0 via the computing device 20 to the system 10 containing a plurality of subsets (four products), i.e., 10A @ $100 per unit, 10B @ $100 per unit, 100 @ $100 per unit, and 10D @ $100 per unit. Based on the order and the supply information of the system 10, the system 10 makes a number of deductions using the processor 12, when the order is received, at Step 100. In this scenario, the system 10 has received supply information from Suppliers 0-3, which respectively have supplies of: 100 @ $100 per unit and 10D @ $99 per unit; 10A @ 110 per unit and 10B @110 per unit; 10A @ 110 per unit and 10B @110 per unit; and 7D @ $100 per unit. At Step 110, the system 10 groups each of the suppliers into one of a plurality of classes, each a product fulfillment count PFC or "bucket," based on best match, and attempts to match one or more subsets of the order with all of the suppliers contained in the memory 14. As illustrated, the system 10 is configured to group buckets based on ability to fill the order, with bucket 2 ranked highest and bucket 0 ranked lowest because there is no perfect match for the supplier within bucket 0, as further discussed hereafter.

Figure 8:
FIG. 8 illustrates another example display provided to a user via a display of a computing device of the user according to an embodiment of the present inventive concept.

At Step 120, the system 10 deduces that Supplier 1 and Supplier 2, both in bucket 2, can both fill one or more subsets, i.e., 10A @ 110 per unit and 10B @110 per unit. To select from these identical supplies, the system 10 randomly selects Supplier 2, at Step 130. This selection causes Supplier 2 to receive a notification from the System 10 to fill 10A and 10B of the order, e.g., as illustrated by FIG. 8, and a portion or two subsets of the order satisfied by Supplier 2 are removed from the order by the system 10, at step 140.

At step 150, Supplier 1 is randomly selected from the bucket 2 to fill one of the remaining subsets, i.e., 100, but it is determined by the system 10 that Supplier 1 can only fill 0C. Thus, the system 10 marks the bucket 2 as empty, a next bucket, i.e., bucket 1 is selected, and Supplier 0 is selected to fill 100 and a notification is sent as previously described, and Supplier 0 is determined that Supplier 0 can only fill 10D @ $99 per unit, which fails the order price constraint, at Step 160. Thus, the system 10 does not utilize Supplier 0 to fill the order for 10D @ $100 and another portion or one subset of the order satisfied by Supplier 0 is removed from the order by the system 10.

At step 170, bucket 0 is selected, e.g., using a randomizer of the system 10, and the system 10 determines that Supplier 3 cannot fill an entirety of any remaining subsets of the order. At step 180, all remaining suppliers are analyzed to determine whether one or more of the remaining suppliers can satisfy an entirety of one or more of the remaining subsets of the order at the price per unit requested by the user. If so, the system 10 processes such as previously described. If not, the system 10 attempts to fill portions of the remaining subsets of the order via all of the suppliers, at step 190. For this scenario, the system 10 determines that no suppliers can fill the entirety of one or more of the remaining subsets of the order at the price per unit requested by the user. Thus, at step 200, it is determined that Supplier 3 can supply 7D @ $100 and Supplier 3.

At steps 210A and 210B, the order is split into two orders, i.e., a partial order and a new order, to allow the user to proceed with both orders. Supplier quantities are updated in view of the orders, at step 220, and the user is presented with a request for input via the computing device 20 with respect to the new order, at step 230. As illustrated, the user selects the new order, which causes a second order to be placed at step 235. In this manner, the system 10 allows the user to select: (i) the partial order only; (ii) the partial order and the new order; and/or (iii) not to proceed with any of the orders. At step 240, both orders are processed by the system 10 as previously discussed.

Turning to FIG. 16, the system 10 is configured to track various metrics of the blood products across the system 10, collect data from one or more users of the system 10, and report analytical information to the one or more users. For instance, the system 10 is configured to use collected data to produce one or more sets of analytics tools that are presented in context in the product. These tools may be used by the user to inform and suggest decisions on when to procure and sell one or more blood products. Such collected data may be used to report a variety of metrics including, but not limited to, daily product pricing averages, supply by geography, demand by geography, price by region, supply channels and/or product flow, average fulfillment time per organization and/or average makeup of orders, average turnaround time, market highs/lows, product highs/lows, total quantities procured/supplied, system supply to system average, e.g., derivatives of all time, a delta between original orders and fulfilled orders, percent of first request success, percent of stock, stat, and/or recurring orders, percent of growth of the system 10, e.g., supply transacted, most/least demanded products, e.g., product, antigen, and/or process, most popular shipping company, ratings, most versatile suppliers, highest touch point suppliers/level of interaction with system, percent orders flagged total by user, by place, and/or by supply/buy, user data, e.g., bounce rates, and/or time of each user on each page or "who is doing what", and/or average quantities transacted per product.

The analytics provided by the system 10 enable an administrator or the system 10 to use data to produce buying/selling recommendations based on aggregated data that may be viewable only by the administrator. Such data may be displayed in context to non-administrator user, thereby allowing them to make more educated business decisions. It is foreseen that the system 10 may be configured to utilize quantities, e.g., procured, sold, and/or other use of the system by a user to trigger access to such data as an added benefit and incentive for the user to utilize the system 10. Likewise, it is foreseen that a limited number of users may have access to such data based on their subscription tier of the system 10.

It is foreseen that the system 10 may be configured to accommodate one or more custom supplies for a supplier and/or purchaser via an "add custom supply" feature. For instance, the system 10 may be configured to allow a supplier to sell or re-sell products that are rare, unique, or have already had processes and antigens added. It is foreseen that the system 10 may be configured to generate invoices and be equipped with various features to facilitate invoicing, e.g., view, manage, process, analyze, and/or export an invoice based on supply and procure. It is foreseen that the system 10 may be configured to provide detailed assistance to new users during initial use via step by step online on-boarding of new buyers and sellers, integrated application and review process to onboard new buyers and sellers, and/or the like. It is foreseen that the system 10 may be configured to provide various management tools to an administrator or other user of the system 10 including, but not limited to, manage, create, edit, delete, privilege, users of their system. For example, an administrator of a hospital system can create and manage both a user and/or a place and may provide a secondary fast track application process using the system 10. The system 10 may be configured to allow a user to build a hierarchy structure with differing levels of access, e.g., various layers for a hospital system, to manage multiple sites, see and pull data from each individually and collectively and compare both to national market trends.

The system 10 is configured to trace and provide one or more histories of the user based on one or more past entries of the user to the system 10. The system 10 is configured to track and report order fill rate metrics, e.g., what percentage of orders are filled via a first order, without requiring any secondary orders when the first order cannot be completely filled. In view of these tracked and reported metrics, the system 10 can be configured to prompt an administrator when the system 10 has a low supply with respect to one or more blood products in view of a predetermined desired supply that is stored in the system 10. In such a scenario, the system 10 may trigger one or more communications, e.g., advertisements, to be sent to one or more suppliers, e.g., a blood bank, to request one or more blood products that are indicated by the system 10 to be in low supply. The system 10 is configured to provide recommendations to the user based on tracked metrics. Such recommendations may include, but are not limited to, when is an ideal time and/or less ideal time to purchase one or more blood products in view of an oversupply and/or an under supply.

In this manner, the present inventive concept provides a computerized system and method that provides a user with an online portal for real-time matching of a blood order to a blood supplier based on a variety of variables tracked by the system including real-time marketplace trend statistical analysis, and without any bias via a blind auction. The system 10 provides a blood product inventory management system for buyers and sellers and is configured to analyze supply and demand in real-time, providing users of the system 10 with data to integrate smart buying and selling capabilities. The system 10 provides a system to manage all product inventories for buyers and sellers, with product inventories integrated into product availability and need. The system 10 is configured to automatically order for users when supply is low. The system 10 is configured to automatically add units to sell when supply is high. The system 10 is configured to adjust pricing and inventory on the exchange in order to eliminate outdating and maximize efficiency of the ecosystem. The system 10 is configured to automatically factor in historical data, e.g., local and/or national, weather data, current events data, and/or medical trend data to produce recommendations on blood draw (pre supply) and planning for procurement (pre-need/more than 45 days out for RBC's for example). The system 10 is configured to integrate predictive data maddening output into the decision making process of the algorithm. For example, the system 10 may identify weather data, e.g., via a computer connected to a communication source, that indicates a large storm in the North Eastern United States, and cross-reference that data with supply that is currently located in that area. The system 10 may be configured to anticipate that there could be a large need for O– and AB+ due to lack of current inventory, and initiate buys or recommendations to buy to top off inventory at one or more hospitals in that area before the storm hits the area. Simultaneously, the system 10 may send a communication to one or more blood centers that there will be a post-storm lack of these same products, and present the one or more blood centers with optimal times to begin campaigns to solicit new donors to fill the predicted need.

In the foregoing description, the present inventive concept is described with reference to specific exemplary embodiments thereof. It will, however, be evident that various modifications and changes may be made thereto without departing from the broader spirit and scope of the present inventive concept as set forth in the appended claims.

This description of the present inventive concept is provided to enable any person skilled in the art to make or use the present inventive concept. Various modifications will be readily apparent to those skilled in the art, and the generic principles defined herein may be applied alternatively without departing from the spirit or scope of the present inventive concept. Thus, the present inventive concept is not intended to be limited to the description herein but is to be accorded the widest scope consistent with the principles and novel features disclosed herein.

The steps of a method, system, or operation described in connection with the present inventive concept disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

Having now described the features, discoveries, and principles of the present disclosure, the manner in which embodiment of the present disclosure are constructed and used, the characteristics of the construction, and advantageous, new and useful results obtained; the new and useful structures, devices, elements, arrangements, parts and combinations, are set forth in the appended claims.

The following claims are intended to cover all of the generic and specific features of the present disclosure herein described, and all statements of the scope of the present inventive concept, which, as a matter of language, might be said to fall there between.

What is claimed is:

1. A method comprising:
   receiving a biological material order over a network, the biological material order being associated with an order facility and specifying demand biological material units;
   identifying a plurality of suppliers each having one or more supply biological material units;
   automatically grouping the plurality of suppliers into a plurality of classes based on a comparison of the demand biological material units with the one or more supply biological material units for each of the plurality of suppliers; and
   automatically generating a match of the demand biological material units of the biological material order to a particular supplier by randomly selecting the particular supplier from a class of the plurality of classes, the particular supplier filling the biological material order by shipping the demand biological material units to the order facility.

2. The method of claim 1, wherein the demand biological material units include at least one of blood products, blood, red blood cells, white blood cells, platelets, plasma, cryoprecipitate, bone, or tissue.

3. The method of claim 1, wherein the class of the plurality of classes includes a subset of the plurality of suppliers.

4. The method of claim 3, wherein the plurality of classes is ranked, the class having a highest ranking of the plurality of classes.

5. The method of claim 4, wherein each of the plurality of classes is ranked based on an ability to fulfill the biological material order.

6. The method of claim 1, wherein the comparison of the demand biological material units with the one or more supply biological material units for each of the plurality of suppliers comprises determining product fulfillment count.

7. The method of claim 1, wherein the plurality of suppliers is further grouped into the plurality of classes based on one or more demand variables of the demand biological material units and one or more supply variables of the supply blood products units.

8. The method of claim 1, further comprising:
generating one or more metrics based on at least one of: the one or more demand variables, the one or more supply variables, the biological material order, the match, or one or more parameters of the arrival of the demand biological material units at the order facility.

9. The method of claim 1, further comprising:
automatically removing the demand biological material units from the biological material order following the match to the particular supplier.

10. One or more non-transitory computer-readable data storage media comprising instructions that, when executed by at least one computing unit of a computing system, cause the computing system to perform operations comprising:
receiving a biological material order, the biological material order being associated with an order facility and specifying demand biological material units;
identifying a plurality of suppliers each having one or more supply biological material units; and
automatically generating a match of the demand biological material units of the biological material order to a particular supplier by randomly selecting the particular supplier from the plurality of suppliers, the plurality of suppliers each having one or more supply biological material units, the particular supplier filling the biological material order by shipping the demand biological material units to the order facility.

11. The one or more non-transitory computer-readable data storage media of claim 10, wherein each of the plurality of suppliers are automatically grouped into one of a plurality of classes based on a comparison of the demand biological material units to the one or more supply biological material units.

12. The one or more non-transitory computer-readable data storage media of claim 10, wherein the particular supplier is randomly selected from a subset of the plurality of suppliers.

13. The one or more non-transitory computer-readable data storage media of claim 12, wherein the subset of the plurality of suppliers is associated with a class of a plurality of classes.

14. The one or more non-transitory computer-readable data storage media of claim 13, wherein the class is selected based on a product fulfillment count.

15. The one or more non-transitory computer-readable data storage media of claim 13, wherein the subset of the plurality of suppliers is identified based on a comparison of one or more demand variables corresponding to the demand biological material units with one or more supply variables corresponding to the supply biological material units.

16. The one or more non-transitory computer-readable data storage media of claim 10, wherein the biological material order further specifies second biological material units, the operations further comprising:
automatically determining that the particular supplier cannot supply the second demand biological material units.

17. The one or more non-transitory computer-readable data storage media of claim 16, the operations further comprising:
automatically generating a random match between the biological material order for the second demand biological material units and a second particular supplier of the plurality of suppliers.

18. The one or more non-transitory computer-readable data storage media of claim 17, wherein the second particular supplier is randomly selected from the plurality of suppliers.

19. The one or more non-transitory computer-readable data storage media of claim 16, the operations further comprising:
generating a new order for the second demand biological material units where none of the plurality of suppliers can supply the second demand biological material units within one or more variables of the biological material order.

20. The one or more non-transitory computer-readable data storage media of claim 19, where the new order matches the second demand biological material units to a second particular supplier of the plurality of suppliers outside the one or more variables of the biological material order.

* * * * *